United States Patent
Wittland et al.

(10) Patent No.: US 10,981,822 B2
(45) Date of Patent: Apr. 20, 2021

(54) DEVICE AND METHOD FOR PRODUCING A MEDICAL GLASS CONTAINER

(71) Applicant: Gerresheimer Bünde GmbH, Bünde (DE)

(72) Inventors: Frank Wittland, Enger (DE); Dirk Schnelle, Bünde (DE)

(73) Assignee: Gerresheimer Bünde GmbH, Bünde (DE)

( * ) Notice: Subject to any disclaimer, the term of this patent is extended or adjusted under 35 U.S.C. 154(b) by 280 days.

(21) Appl. No.: 15/756,475

(22) PCT Filed: Sep. 15, 2016

(86) PCT No.: PCT/EP2016/071760
§ 371 (c)(1),
(2) Date: Feb. 28, 2018

(87) PCT Pub. No.: WO2017/060052
PCT Pub. Date: Apr. 13, 2017

(65) Prior Publication Data
US 2018/0244555 A1    Aug. 30, 2018

(30) Foreign Application Priority Data
Oct. 8, 2015 (DE) .................. 10 2015 117215.1

(51) Int. Cl.
*C03B 23/09* (2006.01)
*A61M 5/28* (2006.01)
(Continued)

(52) U.S. Cl.
CPC ............ *C03B 23/092* (2013.01); *A61M 5/28* (2013.01); *C03B 23/045* (2013.01);
(Continued)

(58) Field of Classification Search
CPC .............................. C03B 23/09; C03B 23/095
See application file for complete search history.

(56) References Cited

U.S. PATENT DOCUMENTS 1,914,205 A * 6/1933 Hooper .................. C03B 23/07
65/26
6,216,493 B1   4/2001 Weston et al.
(Continued)

FOREIGN PATENT DOCUMENTS

WO    2006/039705       4/2006
WO    WO 2006/127843   11/2006
(Continued)

OTHER PUBLICATIONS

European Search Report, dated Dec. 22, 2016, corresponding to International Application No. PCT/EP2016/071760 (filed Sep. 15, 2016), parent of the present application, 5 pp.
(Continued)

*Primary Examiner* — Cynthia Szewczyk
(74) *Attorney, Agent, or Firm* — Leydig, Voit & Mayer, Ltd.

(57) ABSTRACT

A device for producing a high-purity medical glass container from a hollow cylindrical glass blank extending along an axial direction (X) and having at least one open end, wherein the glass blank has a mouldable moulded section extending in the axial direction (X) from the open end. The device comprises a first moulding tool and a second moulding tool, where the first moulding tool has a moulding pin. The moulding pin can be moved via the open end of the hollow cylindrical glass blank in the moulded section thereof along the axial direction (X), wherein the moulding pin is fixed in a fixing unit of the first moulding tool. The moulded section can be deformed by the second moulding tool in such a way that an inner surface of the moulded section is in contact
(Continued)

with the moulding pin, whereby the moulded section forms a channel.

20 Claims, 15 Drawing Sheets

(51) Int. Cl.
  *C03B 23/045* (2006.01)
  *C03B 23/18* (2006.01)
  *A61M 5/31* (2006.01)
(52) U.S. Cl.
  CPC ............ *C03B 23/095* (2013.01); *C03B 23/18* (2013.01); *A61M 5/3129* (2013.01); *A61M 2207/00* (2013.01); *A61M 2207/10* (2013.01)

(56) References Cited

U.S. PATENT DOCUMENTS

| | | |
|---|---|---|
| 6,415,631 B1 | 7/2002 | Weston et al. |
| 2004/0129030 A1 | 7/2004 | Tanada et al. |
| 2004/0231361 A1 | 11/2004 | Moriya et al. |
| 2012/0060558 A1 | 3/2012 | Haselhorst et al. |
| 2013/0095261 A1* | 4/2013 | Ahn .......................... C03C 3/06 428/34.4 |
| 2015/0114043 A1 | 4/2015 | Risch et al. |
| 2015/0197039 A1* | 7/2015 | Matsuzuki ............ C03B 11/122 264/297.7 |

FOREIGN PATENT DOCUMENTS

| | | |
|---|---|---|
| WO | 2012/085619 | 6/2012 |
| WO | WO 2015/004103 | 1/2015 |
| WO | 2017/060052 | 4/2017 |

OTHER PUBLICATIONS

Chinese First Office Action with English translation, dated Jan. 22, 2020, corresponding to Chinese Application No. 201680049901.7, 15 pp.

* cited by examiner new tungsten moulding pin tungsten moulding pin after an operating time of 1 hour new silicon nitride moulding pin silicon nitride moulding pin after an operating time of 2.5 hours

DEVICE AND METHOD FOR PRODUCING A MEDICAL GLASS CONTAINER

CROSS-REFERENCE TO RELATED APPLICATIONS

This application is a U.S. National Stage Application filed under 35 U.S.C. § 371 of International Application No. PCT/EP2016/071760, filed Sep. 15, 2016, which claims the benefit of German Application No. 10 2015 117 215.1, filed Oct. 8, 2015. All of these applications are hereby incorporated by reference in their entireties.

The invention relates to a device for producing a high-purity medical glass container from a hollow cylindrical glass blank extending along an axial direction (X) and having at least one open end, the glass blank having a mouldable moulded section extending in the axial direction (X) from the open end, the device comprising:
  a. a first moulding tool having a moulding pin, the moulding pin being able to be moved via the open end of the hollow cylindrical glass blank in the moulded section thereof along the axial direction (X), the moulding pin being fixed in a fixing unit of the first moulding tool;
  b. a second moulding tool, via which at least the moulded section of the hollow cylindrical glass blank can be deformed, the moulded section being able to be deformed by the second moulding tool in such a way that an inner surface of the moulded section is in contact with the moulding pin, whereby the moulded section forms a channel.

Generic medical glass containers are in particular syringes, but also ampoules or carpules. During new development of medicaments, the first medicament formulation to be analysed is stored in glass ampoules, known as vials. The first stability analyses are conducted in these vials. A glass container which, from a pharmaceutical viewpoint, has the same or very similar properties as the vial originally used prevents undesirable property changes during storage. Glass containers of this kind are desirable in the pharmaceutical industry as containers for sensitive/reactive formulations, since packaging-related, undesirable property changes do not occur.

Prefillable all-glass syringes are generally produced by forming sections of glass tubes (glass blanks), which are used as semi-finished products, and subsequently shaping at high temperatures. During shaping, moulding tools are used which have sufficient resistance to thermoforming and to wear while at the same time having high ductility. The glass syringes are generally produced from highly chemical-resistant and temperature-resistant glass, such as borosilicate glass or quartz glass. Forming the syringe cone is particularly critical in this case. The syringe cone comprises a channel that connects the cannula to the syringe cavity in which the medium to be administered is stored.

The syringe cone may be formed inter alia as what is known as a Luer cone. A Luer taper, Luer lock or Luer slip system is a standardised (ISO Standard 594) connection system for tube systems in the medical field, and ensures compatibility across different producers. Said system is used inter alia in syringes, cannulas and infusion tubes. A male Luer cone is a flat (gradient 6%) hollow cone having a relatively large surface and therefore good adhesion to a connected (female) Luer taper of a cannula for example. The conical structure of the two connecting parts ensures adequate sealing.

Furthermore, glass syringes comprising what are known as staked-in needles (SIN) are also used. In this case, the cannula is usually fixed in the channel by means of an adhesive connection. It is generally necessary for the channel of the SIN syringes to have a smaller diameter than in the case of syringes having a Luer cone, in order to make it easier to glue the cannula in place.

The syringe cone is produced by heating the glass blank in sections. When the glass blank is in a mouldable state, the external shaping is produced using a second moulding tool and the internal shaping is produced by counterholding what is known as a moulding pin, which pin is a component of a first moulding tool.

Whereas the moulding tools on the outside of the tubes are noncritical because any abrasion that may occur does not come into contact with the filling material, all tools that are used inside the glass blank should be considered to be critical. The tools currently used in the prior art consist of almost 100% tungsten. Although this material is good for the tools that are in contact on the outside, it is less suitable for tools that are used inside the glass container. The moulding pin for the channel of the syringe cone is very small and heats up significantly due to the low thermal capacity, and thus oxides result which lead to wear and abrasion. The abrasion of the moulding pin is in an order of magnitude that generally requires the moulding pin to be replaced after approximately 1 hour of operation. At least some of this abraded material is deposited in the channel where it can later be absorbed by the filling material and may result in impairment of the effectiveness and/or tolerability thereof. Dissolved tungsten polyanions in prefilled syringes interact with some proteins such that said proteins aggregate. This results in particle formation and a change in the effectiveness of the pharmaceutical drug or of endogenous proteins. In particular, new biotechnological active substances often comprise long-chain molecule chains which are very sensitive in terms of interaction with trace elements. These products therefore cannot be stored in normal syringes. The residues, due to the abrasion, can be detected by means of an extraction process and subsequent analytical determination. Permissible threshold values have already been agreed upon, on the basis of incidents of intolerance in industry. According thereto, syringes having a tungsten content of <50 ng are currently referred to as high-purity syringes. Standard syringes, in contrast, can have a value of between 500 and 2500 ng. Solutions are currently provided in industry by means of washing processes or replacement metal such as platinum. However, these solutions can only reduce the content or introduce a replacement metal which in turn may also not be without interactions.

Alternative materials for moulding pins of this kind must be highly temperature-resistant and highly resistant to temperature changes (thermal shock resistance). Moreover, the material should have little tendency to adhere to the glass blank during moulding. Many of the possible materials are much more brittle than metal materials. Up to now, the moulding pins have been fixed in a fixing unit. In this case, the moulding pin is arranged in a bore of the fixing unit. Moreover, the moulding pin is fixed by a fixing screw that is in point contact with the moulding pin. Point contact of this kind means that more brittle moulding pins can break easily.

The object of the present invention is therefore to provide a device and a method for producing high-purity syringes which have no or a low content of tungsten, the device making it possible to use more brittle moulding pins.

In one aspect, this object is achieved by a device for producing a high-purity medical glass container from a hollow cylindrical glass blank extending along an axial direction (X) and having at least one open end, the glass blank having a mouldable moulded section extending in the axial direction (X) from the open end, the device comprising:

a. a first moulding tool having a moulding pin, the moulding pin being able to be moved via the open end of the hollow cylindrical glass blank in the moulded section thereof along the axial direction (X), the moulding pin being fixed in a fixing unit of the first moulding tool;

b. a second moulding tool, via which at least the moulded section of the hollow cylindrical glass blank can be deformed, the moulded section being able to be deformed by the second moulding tool in such a way that an inner surface of the moulded section is in contact with the moulding pin, whereby the moulded section forms a channel.

The device is characterised in that the fixing unit has at least two jaw-type elements which can be pressed extensively on the moulding pin, whereby the moulding pin can be force-lockingly fixed.

The embodiment according to the invention of the fixing unit thus prevents point fixing of the moulding pin. The moulding pin is now clamped between two jaw-type elements and rests extensively on said elements in sections, such that force-locking fixing results. Moulding pins that have a smaller diameter and that are more brittle can also be fixed in a fixing unit of this kind without being damaged or breaking due to the fixing.

The jaw-type elements of the fixing unit are preferably formed in one piece.

According to a preferred concept of the invention, the fixing unit extends along an axial direction (X') and has a first section, a second section and a third section. The second and the third section are preferably formed as circular cylinders. The fixing unit preferably has a first through bore that extends along an axial central axis of the fixing unit and in which the moulding pin can be arranged at least in sections. In this case, the moulding pin can be arranged so as to protrude beyond the first section. Said protruding section is moved via the open end of the glass blank in the moulded section when the moulded section of said glass blank is deformed. The moulded section is then deformed by the second moulding tool in such a way that an inner surface of the moulded section is in contact with the section of the moulding pin located in the moulded section, whereby the moulded section of the glass blank forms a channel.

According to a further preferred concept of the invention, the second section has a first and a second slot. In this case, the jaw-type elements are spaced apart by means of said first and the second slot. The first slot is preferably arranged in a first plane that is spanned by a first vector in the axial direction (X') and by a second vector in the radial direction (Y'). The second slot is preferably arranged in a second plane that is spanned by the second vector and by a third vector. The third vector and the first plane enclose an angle α. This angle α is preferably in a range of between 45° and 125°, and is particularly preferably 90°.

Furthermore, the first and the second slot have a common intersection line which extends along the radial direction (Y').

The second section preferably has a first length along the axial direction (X'), the first slot having a second length along the axial direction (X') that is less than the first length.

According to a further preferred embodiment, the fixing unit has a second through bore in the second section, which bore extends in the radial direction (Y'), the second through bore being open towards the first slot and being arranged between the first section of the fixing unit and the first slot in the axial direction.

The second section preferably has a third through bore, the central axis of which is perpendicular to the first plane and is radially off-centre with respect to the axial central axis of the fixing unit. A fastening means can preferably be fastened in said third through bore, which fastening means can reduce a slot width of the first slot, whereby the jaw-type elements can be pressed on the moulding pin. A fastening means of this kind could be a clamping screw for example, by means of which a force is applied to the two jaw-type elements such that said elements are pressed together, whereby the moulding pin is fixed extensively by the jaw-type elements. The off-centre arrangement of the third through bore does not impede the course of the first through bore or of the moulding pin arranged therein. The second through bore promotes leverage between the jaw-type elements. The spacing between the third through bore and the second through bore in the axial direction is preferably selected so as to be as large as possible in order to achieve correspondingly large leverage.

According to a further advantageous concept of the invention, the moulding pin consists of a non-metallic material. Using moulding pins made of non-metallic materials makes it possible to produce high-purity glass syringes which have no or only small tungsten/metal residues. Active substances can sometimes be stored in syringes of this kind for up to 3 years without the active substance being impaired.

The mouldable state of the moulded section is preferably achieved by heating, the temperature being in a range of between 1000° C. and 1200° C., and preferably being approximately 1100° C.

Accordingly, it is advantageous for the materials used for the moulding pin to be temperature-resistant up to 1200° C. and to be highly resistant to temperature changes (thermal shock resistance). Moreover, the material should have little tendency to adhere to the glass blank during moulding. Finally, the material should have an economically justifiable service life to acquisition cost ratio.

Technical ceramics or ceramic-like materials meet these requirements. Accordingly, according to a particularly preferred embodiment of the invention, the moulding pin consists of technical ceramics or of a ceramic-like material. Ceramic materials are polycrystalline, inorganic and non-metallic. Said materials are generally moulded from a raw mixture at room temperature, and obtain their typical material properties by means of a sintering process that takes place at high temperatures. The term "technical ceramics" is the generic term for ceramic materials and products produced therefrom for technical applications. Technical ceramics are further divided into silicate ceramics, oxide ceramics and non-oxide ceramics. The non-oxide ceramics are further differentiated into carbide and nitride non-oxide ceramics.

Although the acquisition cost of technical ceramics-based or ceramic-like materials-based moulding pins is higher than, for example, in the case of tungsten which has been used up to now, said materials allow for significantly longer operating times. Technical ceramics are also preferable to platinum. Although the acquisition costs are comparable, ceramics have longer operating times than platinum. For example, operating times of up to 24 hours have been determined for ceramics-based moulding pins, whereas platinum moulding pins allowed operating times of approximately 8 hours. Tungsten-based moulding pins have operating times of approximately 1 hour.

The moulding pin particularly preferably consists of silicon nitride ($Si_3N_4$) or glass-like carbon. Other preferred materials are zirconium oxide and zirconia reinforced alumina (ZTA). Silicon nitride is a non-oxide ceramic and has a high fracture toughness and a low coefficient of thermal expansion. It exhibited a long-term use temperature of 1300° C. and a comparatively very good resistance to temperature changes. Glass-like carbon or glassy carbon has particularly little tendency to adhere to the glass blank during moulding, but the long-term use temperature is only 600'C. However, this long-term use temperature can be increased to over 2000° C. by using an inert gas atmosphere.

The materials silicon nitride and glass-like carbon are characterised by their high resistance to thermal interactions, and are therefore particularly preferred for use as moulding pins. Since silicon nitride has a higher modulus of elasticity than glass-like carbon, moulding pins made of silicon nitride are less deflectable. This results in a higher shape accuracy of the eccentricity of the cone channel. However, it is also necessary for the moulding pin to be positioned very accurately during the process, in order to prevent the moulding pin from breaking.

According to a preferred concept of the invention, the moulding pin has a frustoconical end region and a cylindrical longitudinal region having a circular cross section. The frustoconical end region prevents the presence of edges on the moulding pin, which can cause marks, creases, etc. in the cone channel. Moreover, the frustoconical end region prevents increased abrasion at the edges of the moulding pin. The moulding pin preferably has a constant first diameter in the longitudinal region. Obviously, said first diameter determines the inner diameter of the channel. Said first diameter is preferably in a range of between 0.7 mm and 1.3 mm, and is particularly preferably approximately 1 mm.

The diameter of the moulding pin has to be adjusted to the specified requirements for the glass container. Since, in the case of SIN syringes, the cannula is fastened or adhesively bonded in the channel, said SIN syringes often require a channel having a smaller diameter compared with Luer cone syringes. The disadvantage of too small a diameter in moulding pins is that said pins are difficult to fasten and break quickly. Accordingly, according to a further preferred embodiment of the invention, the moulding pin has a frustoconical end region, a cylindrical reduced region, and a cylindrical longitudinal region. In this case, the reduced region and the longitudinal region have a circular cross section.

The longitudinal region preferably has a first diameter that is larger than the second diameter of the reduced region. The moulding pin can thus be fastened at the longitudinal region, which has the larger diameter and is therefore more stable. At the same time, the reduced region can form a channel having a smaller diameter. The reduced region can extend over the entire length of the channel, whereby a channel having a constant diameter is formed. It would also be conceivable, however, for the reduced region to extend over only a section of the channel length. Accordingly, a channel having two different diameters would be formed.

In the field of SIN syringes, it is advantageous for the channel to have a distal section having a larger inner diameter. The needle is inserted and fastened or adhesively bonded in said distal region. The transition region to the section having the smaller diameter can function as a contact surface for the needle. Accordingly, it is possible to produce syringes having a constant effective needle length. Furthermore, it would also be conceivable for the moulding pin to have a plurality of reduced regions having different diameters. The first diameter is preferably in a range of between 0.7 and 1.3 mm, and is particularly preferably approximately 1 mm. The second diameter is preferably in a range of between 0.45 mm and 0.9 mm, and is particularly preferably approximately 0.7 mm.

The moulding pin preferably has a transition region between the longitudinal region and the reduced region. The diameter of the moulding pin preferably tapers continuously in said transition region.

According to a preferred concept of the invention, the hollow cylindrical glass blank is arranged on a retaining device in such a way as to be rotatable, the axis of rotation being an axial central axis of the glass blank. The rotation of the glass blank during moulding ensures uniform deformation of the glass blank.

The second moulding tool preferably has two mutually spaced shaping rollers. In this case, the shaping rollers are spaced apart by a first spacing in a first position, at least the moulded section of the hollow cylindrical glass blank being able to be moved between the shaping rollers when the shaping rollers are in the first position.

The shaping rollers can preferably be moved into a second position in which said rollers are spaced apart by a second spacing that is smaller than the first spacing. In this case, in the second position the shaping rollers can apply a deformation force to the moulded section of the hollow cylindrical glass blank, whereby an outer shaping of the moulded section can be achieved. An inner shaping of the moulded section can be achieved by the moulding pin of the first moulding tool.

According to a further preferred concept of the invention, the device has a cooling means that can cool the moulding pin. Corresponding cooling of the moulding pin can increase the operating time thereof.

In a further aspect, the object of the invention is also achieved by a method for producing a medical glass container having high-purity inner surfaces, said method comprising the following steps:
  a. providing a hollow cylindrical glass blank extending along an axial direction (X) and having at least one open end, the glass blank having a mouldable moulded section extending in the axial direction (X) from the open end, which section is in a mouldable state;
  b. providing a first moulding tool having a moulding pin, the moulding pin being fixed n a fixing unit of the first moulding tool;
  c. providing a second moulding tool, via which at least the moulded section of the hollow cylindrical glass blank can be deformed;
  d. inserting the moulding pin via the open end of the hollow cylindrical glass blank in the moulded section thereof;
  e. deforming the moulded section by the second moulding tool in such a way that an inner surface of the moulded section is in contact with the moulding pin, whereby the moulded section forms a channel.

The method is further characterised in that the moulding pin is fixed in a fixing unit of the first moulding tool, the fixing unit having at least two jaw-type elements which can be pressed extensively on the moulding pin, whereby the moulding pin is force-lockingly fixed. In this case, the jaw-type elements of the fixing unit are preferably formed in one piece.

The method preferably makes use of a fixing unit that extends along an axial direction (X') and has a first section, a second section that is formed as a circular cylinder, and a third section that is formed as a circular cylinder. The fixing unit preferably has a first through bore that extends along an axial central axis of the fixing unit and in which the moulding pin can be arranged at least in sections. The moulding pin can advantageously be arranged so as to protrude beyond the first section.

The second section of the fixing unit that is used preferably has a first and a second slot, the jaw-type elements being spaced apart by means of the first and the second slot. In this case, the first slot is preferably arranged in a first plane that is spanned by a first vector in the axial direction (X') and by a second vector in the radial direction (Y'). It is furthermore advantageous for the second slot to be arranged in a second plane that is spanned by the second vector and by a third vector, the third vector and the first plane enclosing an angle α. This angle α is preferably in a range of between 45° and 125°, and is particularly preferably 90°. Furthermore, the first and the second slot have a common intersection line which extends along the radial direction (Y').

According to a further concept of the invention, the second section of the fixing unit used in the method has a first length along the axial direction (X"), the first slot having a second length along the axial direction (X') that is less than the first length.

The fixing unit that is used preferably has a second through bore in the second section, which bore extends in the radial direction (Y'). The second through bore is preferably open towards the first slot and is arranged between the first section of the fixing unit and the first slot in the axial direction.

The mouldable state of the moulded section is advantageously achieved by heating, the temperature being in a range of between 1000° C. and 1200° C., and preferably being approximately 1100° C.

The moulding pin that is used preferably consists of technical ceramics or a ceramic-like material. The moulding pin particularly preferably consists of silicon nitride ($Si_3N_4$) or glass-like carbon.

According to a further preferred concept of the invention, the method makes use of a moulding pin that has a frusto-conical end region and a cylindrical longitudinal region having a circular cross section. In this case, the moulding pin has a constant first diameter in the longitudinal region. The first diameter is preferably in a range of between 0.7 mm and 1.3 mm, and is preferably approximately 1 mm.

According to a further preferred concept of the invention, the method makes use of a moulding pin that has a frusto-conical end region, a cylindrical reduced region, and a cylindrical longitudinal region. In this case, the reduced region and the longitudinal region have a circular cross section. The longitudinal region preferably has a first diameter that is larger than the second diameter of the reduced region. The first diameter is preferably in a range of between 0.7 and 1.3 mm, and is particularly preferably approximately 1 mm. The second diameter is preferably in a range of between 0.45 mm and 0.9 mm, and is particularly preferably approximately 0.7 mm. The moulding pin preferably has a transition region between the longitudinal region and the reduced region. The diameter of the moulding pin preferably tapers continuously in said transition region.

According to an advantageous concept of the invention, the hollow cylindrical glass blank is arranged on a retaining device and is rotated during deformation. In this case, the axis of rotation is an axial central axis of the hollow cylindrical glass blank.

The second moulding tool advantageously has two mutually spaced shaping rollers, the shaping rollers being spaced apart by a first spacing in a first position. When the shaping rollers are in the first position, preferably at least the moulded section of the hollow cylindrical glass blank is moved between the shaping rollers.

According to a further advantageous concept of the invention, the shaping rollers are moved into a second position in which said rollers are spaced apart by a second spacing that is smaller than the first spacing. In said second position, the shaping rollers apply a deformation force to the moulded section of the hollow cylindrical glass blank. An outer shaping of the moulded section can be achieved thereby. An inner shaping of the moulded section is advantageously achieved by the moulding pin of the first moulding tool.

The moulding pin is preferably cooled by a cooling means.

Further advantages, aims and properties of the present invention will be explained in the following description of the accompanying drawings. Similar components may have the same reference signs in the various embodiments.

Figure 1:
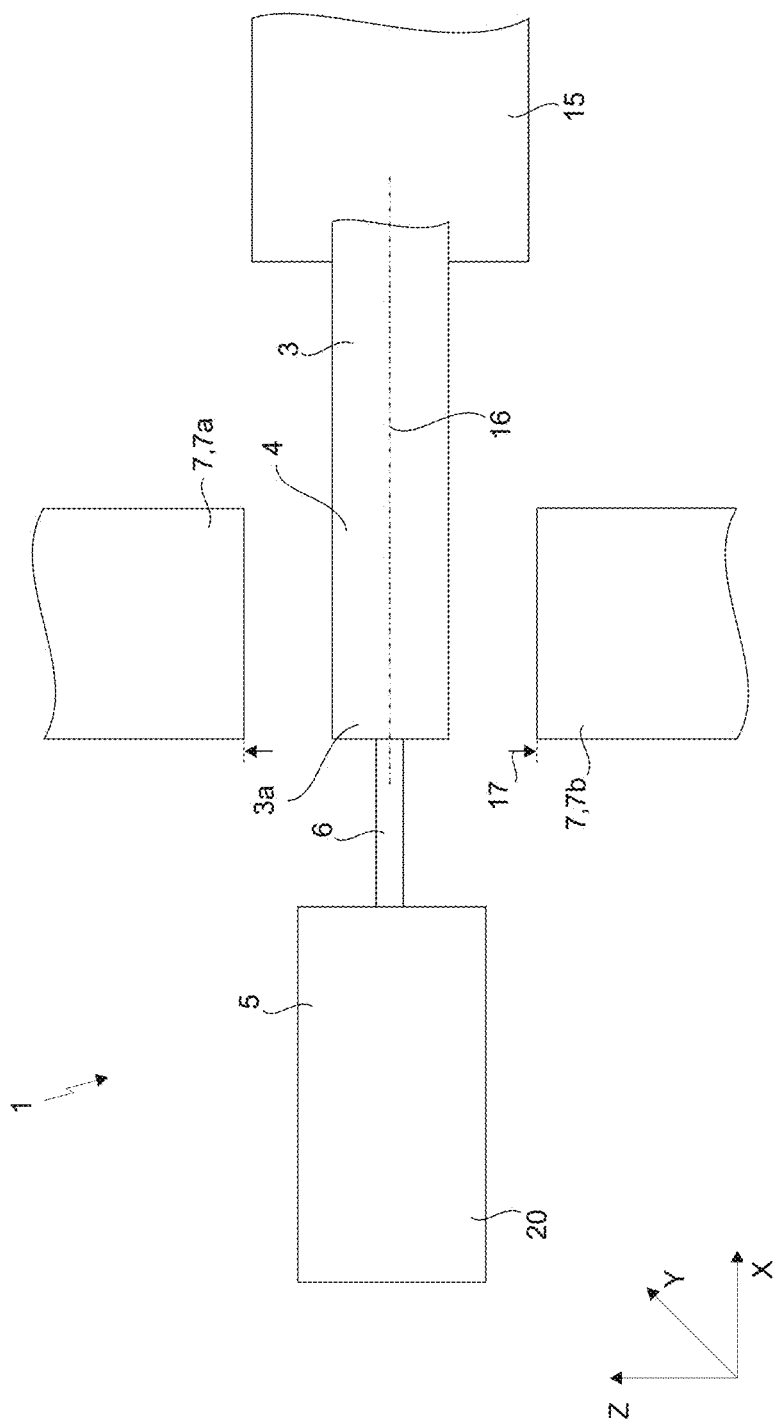
FIG. 1 shows a schematic arrangement of a device for producing a medical glass container.
Figure 2:
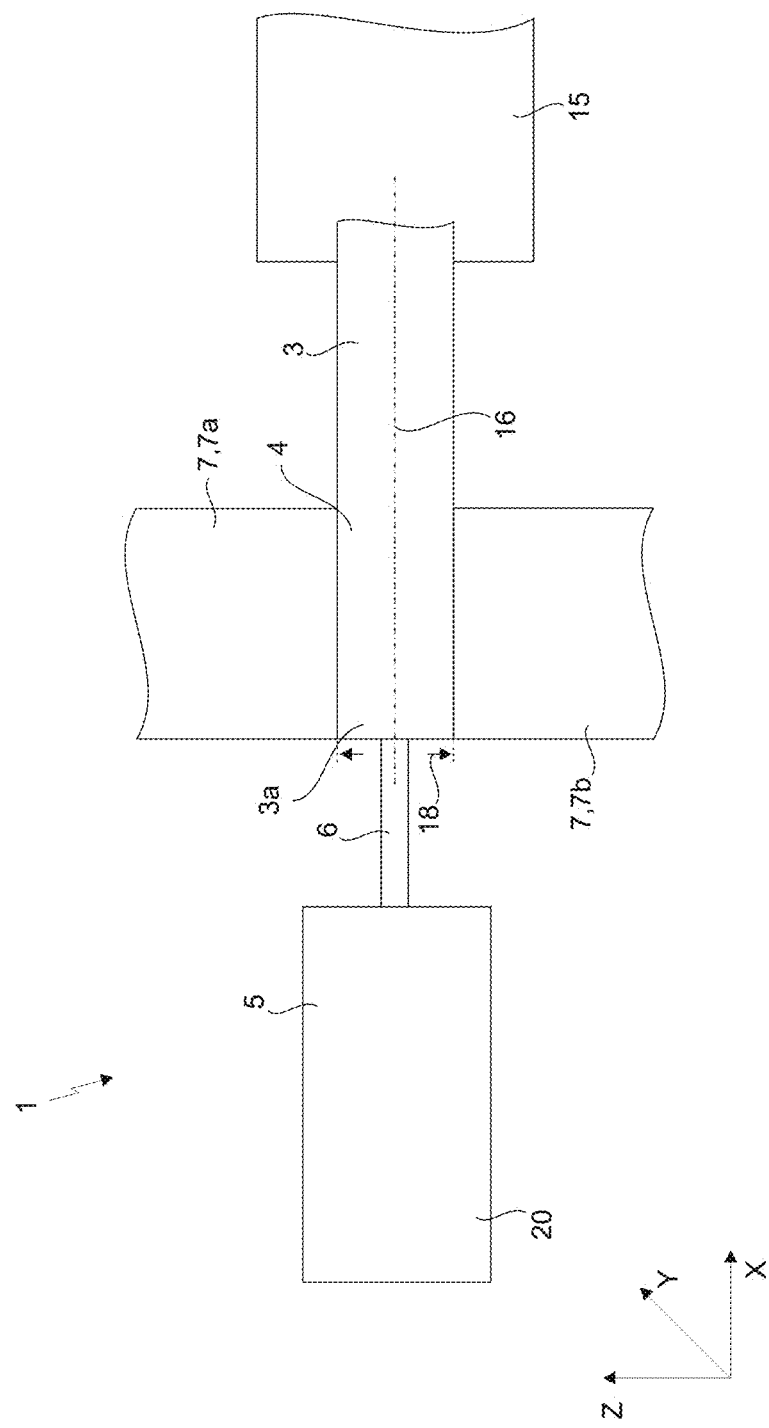
FIG. 2 shows a schematic arrangement of a device for producing a medical glass container.
Figure 18:
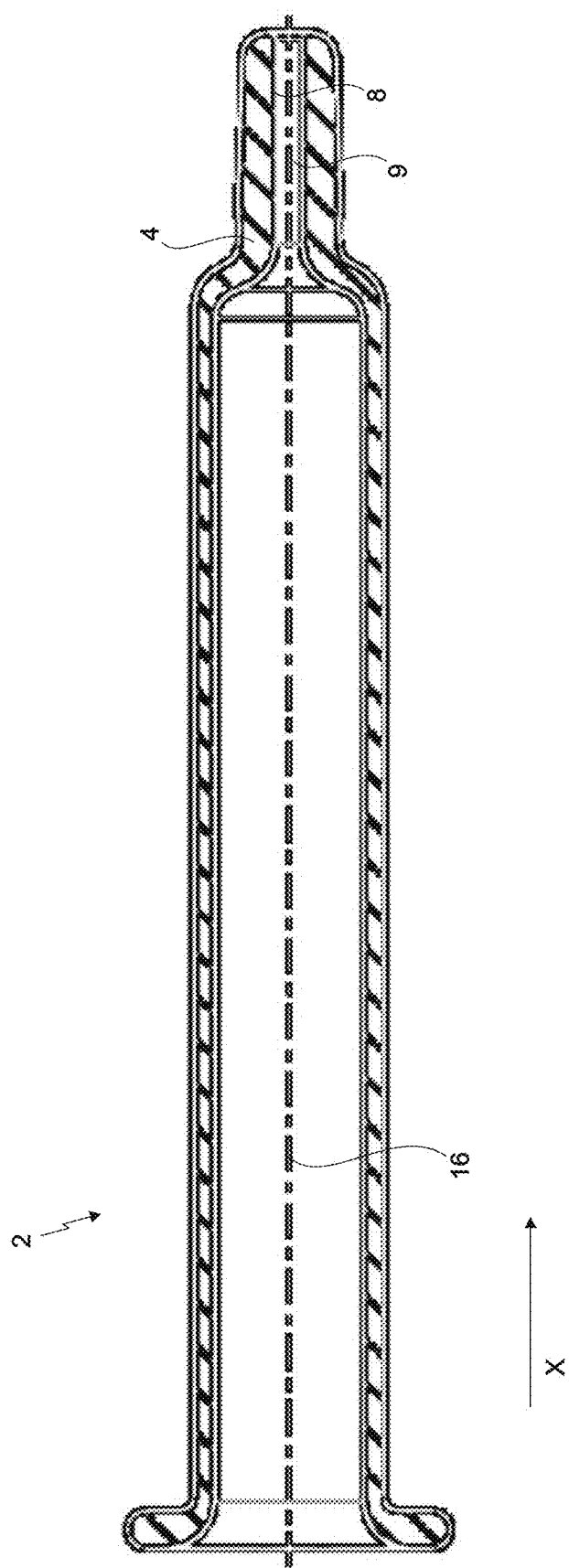
FIG. 18, 18a are sectional views of a syringe manufactured from a glass blank.
Figure 18A:
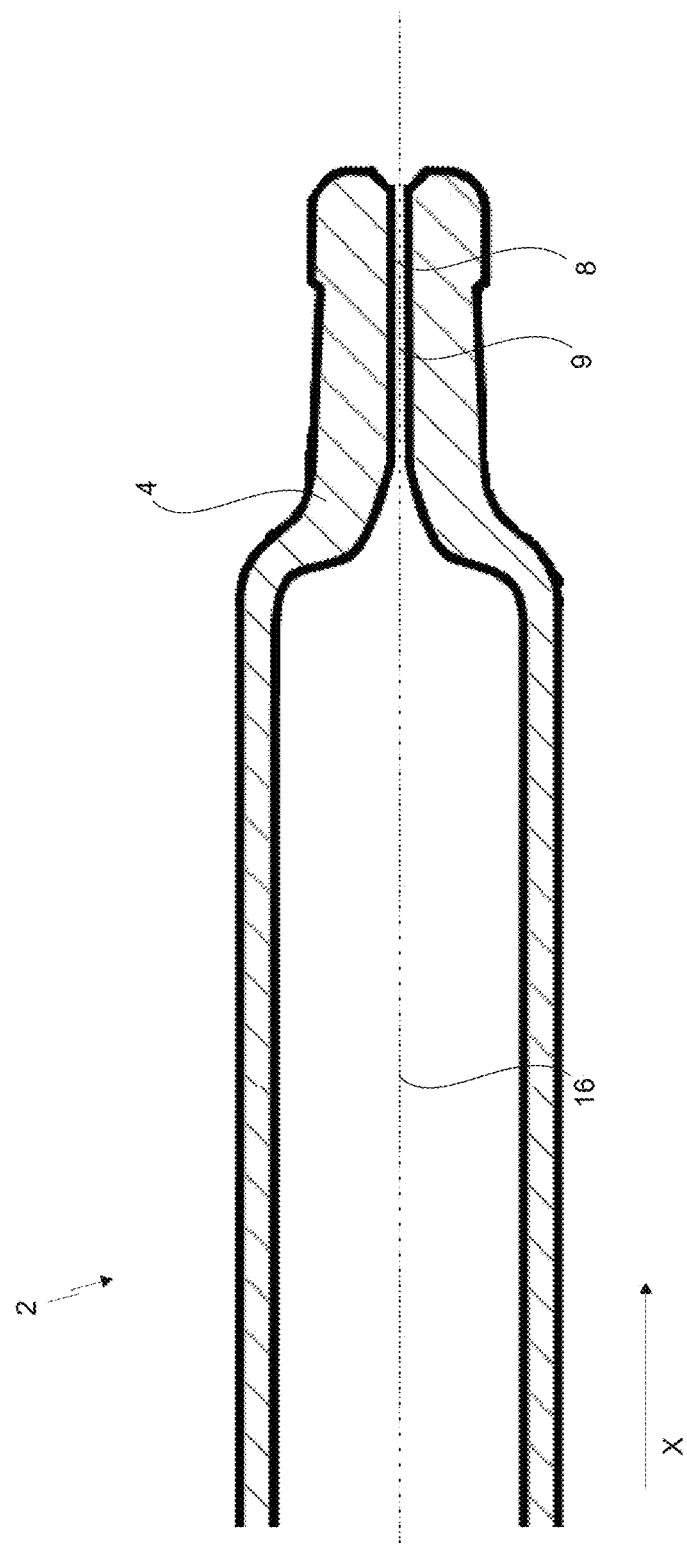
Figure 19A:
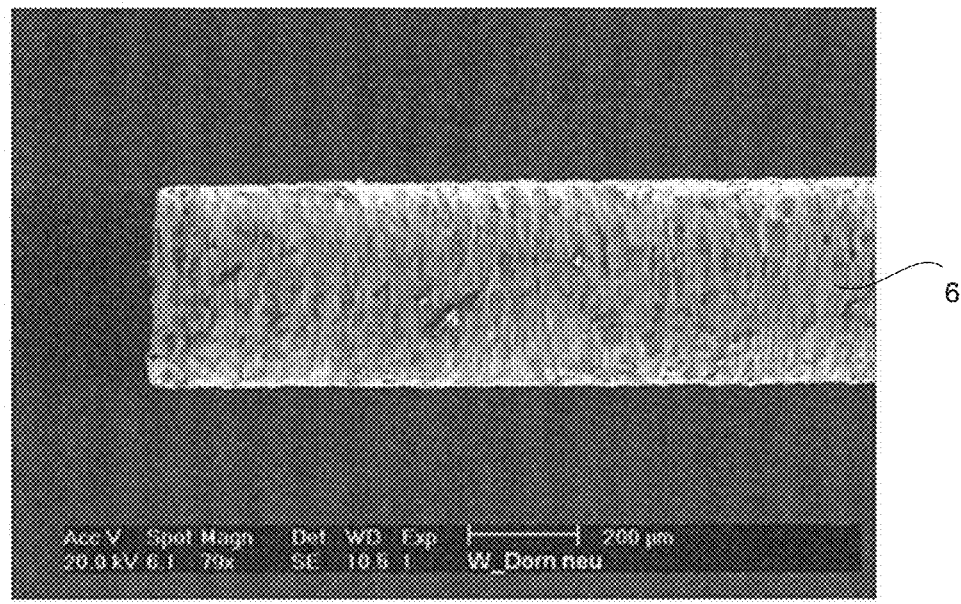
FIG. 19a is a microscope image of a new tungsten moulding pin.
Figure 19B:
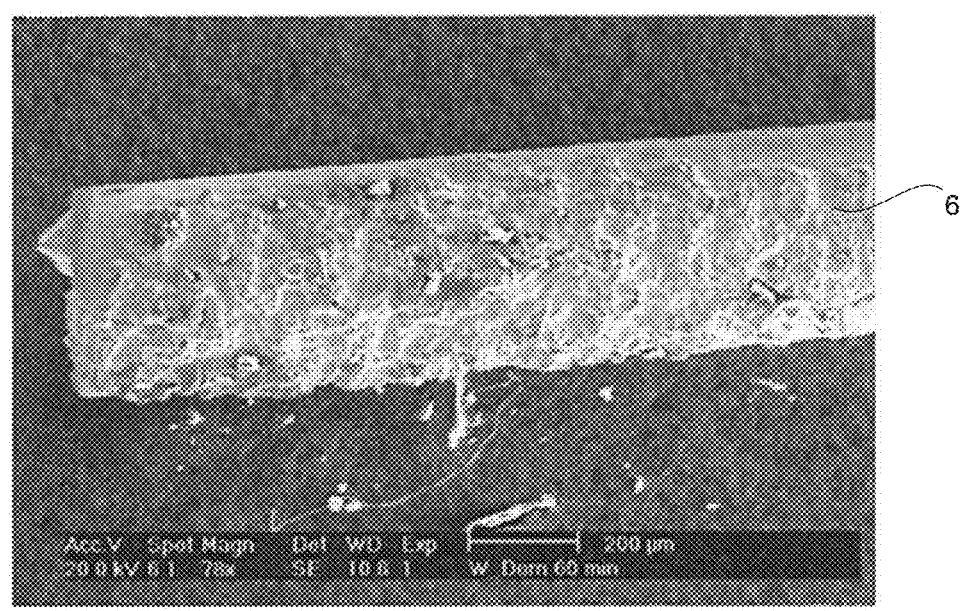
FIG. 19b is a microscope image of a tungsten moulding pin after an operating time of 1 hour.
Figure 19C:
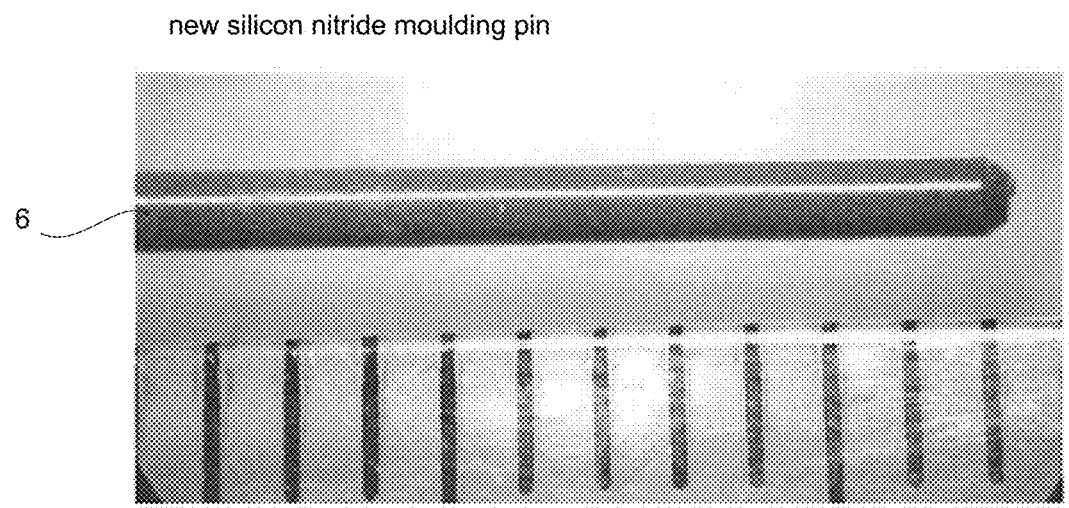
FIG. 19c is a microscope image of a new silicon nitride moulding pin.
Figure 19D:
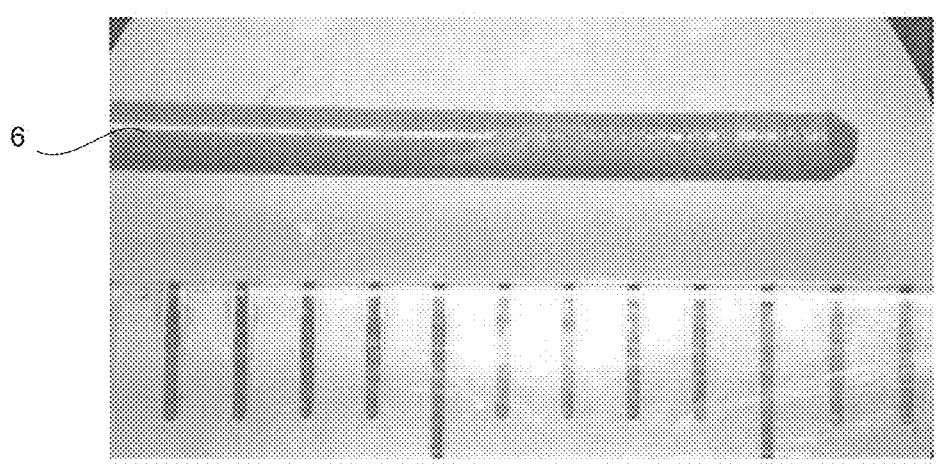
FIG. 19d is a microscope image of a silicon nitride moulding pin after an operating time of 2.5 hours.

FIGS. 1 and 2 show a schematic arrangement of a device (1) for producing a medical glass container (2) having high-purity inner surfaces. A glass container (2) of this kind is shown in FIGS. 18 and 18a for example, and is produced from a hollow cylindrical glass blank (3) extending along an axial direction (X) and having at least one open end (3a). Said glass blank (3) has a mouldable moulded section (4) extending in the axial direction (X) from the open end (3a), which section is in a mouldable state. The mouldable state is generally achieved by heating the glass, the temperature being in a range of between 1000° C. and 1200° C., and preferably being approximately 1100° C. The hollow cylindrical glass blank (3) is arranged on a retaining device (15) in such a way as to be rotatable, the axis of rotation being an axial central axis (16) of the hollow cylindrical glass blank (3). Rotating the glass blank ensures uniform deformation thereof.

The device (1) further comprises a first moulding tool (5) having a moulding pin (6). Said moulding pin (6) preferably consists of a non-metallic material, preferably technical ceramics or a ceramic-like material, and particularly preferably of silicon nitride ($Si_3N_4$) or glass-like carbon. The moulding pin (6) is fixed by means a fixing unit (20) of the first moulding tool (5) and can be moved via the open end (3a) of the hollow cylindrical glass blank (3) in the moulded section (4) thereof along the axial direction (X). The fixing unit (20) has at least two jaw-type elements (21, 22) which can be pressed extensively on the moulding pin (6), whereby the moulding pin (6) is force-lockingly fixed. For this purpose, the first moulding tool (5) has a translation unit which moves the fixing unit (20) and/or the moulding pin (6) along the axial direction (X).

The device (1) further has a second moulding tool (7), via which at least the moulded section (4) of the hollow cylindrical glass blank (3) can be deformed. The moulded section (4) can be deformed by the second moulding tool (7) in such a way that an inner surface (8) of the moulded section (4) is in contact with the moulding pin (6), whereby the moulded section (4) forms a channel (9). The second moulding tool (7) has two mutually spaced shaping rollers (7a, 7b). In the configuration shown in FIG. 1, the shaping rollers (7a, 7b) are in a first position, in which they are spaced apart by a first spacing (17). When the shaping rollers (7a, 7b) are in said first position, at least the moulded section (4) of the hollow cylindrical glass blank (3) can be moved between the shaping rollers (7a, 7b). This can be achieved by means of a corresponding transport device for example, which feeds glass blanks to the device (1) and, after processing, transports said blanks to the next manufacturing step.

In the configuration shown in FIG. 2, the shaping rollers (7a, 7b) are in a second position. In said second position, the shaping rollers (7a, 7b) are spaced apart by a second spacing (18). Said second spacing (18) is smaller than the first spacing (17). The shaping rollers are in contact with the moulded section (4) of the glass blank (3), whereby a deformation force is applied to the moulded section (4). An outer shaping of the moulded section (4) is thus achieved. The inner shaping of the moulded section (4) and/or the shaping of the channel (9) is achieved by counterholding the moulding pin (6). In this case, the shape of the channel (9) is dependent on the shape of the moulding pin (6). In order to increase the operating times of the moulding pin, it is advantageous for the device (1) to have a cooling means that can cool the moulding pin (6).

Figure 3:
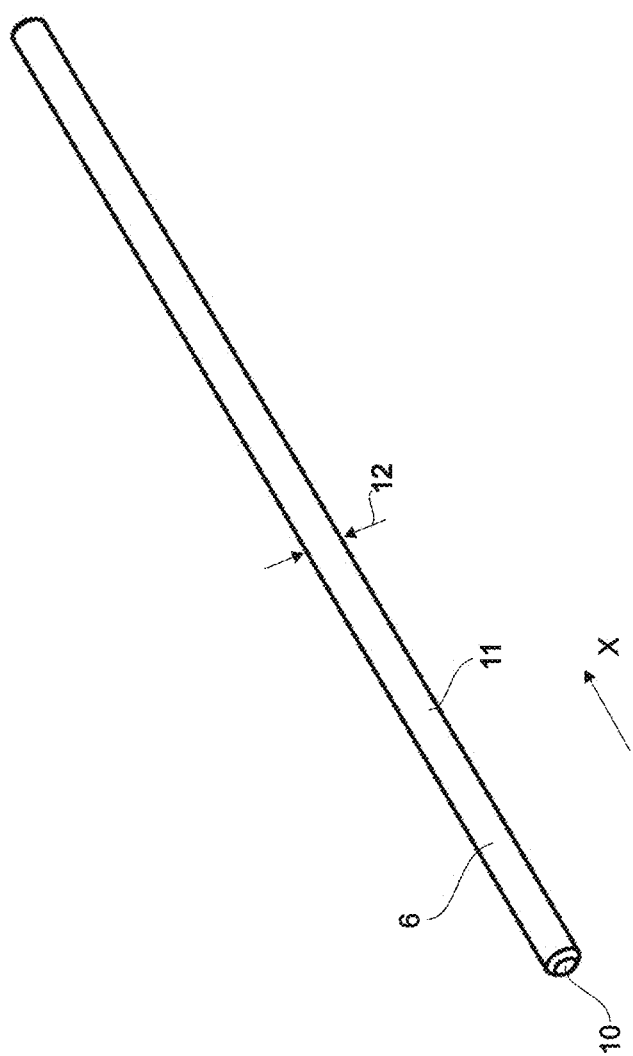
FIG. 3 is an isometric view of a moulding pin.

FIG. 3 shows a moulding pin (6) according to a first embodiment. The moulding pin (6) has a frustoconical end region (10) and a cylindrical longitudinal region (11). Both regions have a circular cross section. The moulding pin (6) has a constant first diameter (12) in the longitudinal region (11). Said first diameter (12) can be selected according to the corresponding channel diameter requirements. When a moulding pin (6) of this kind is used, a channel (9) having a constant diameter is formed.

Figure 4:
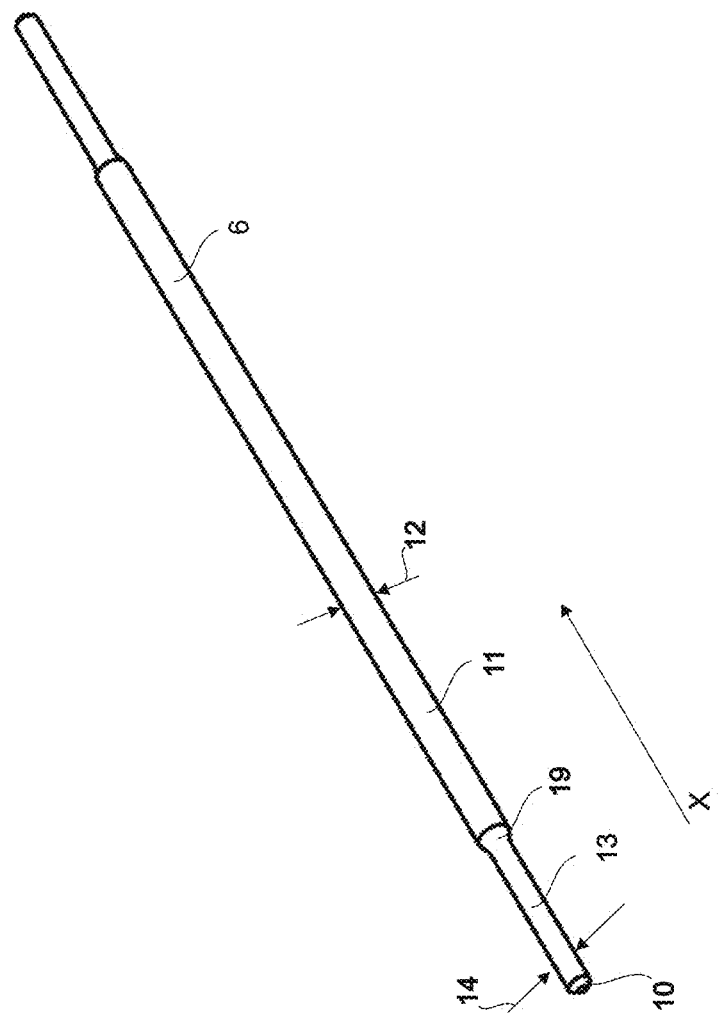
FIG. 4 is an isometric view of a moulding pin according to a further embodiment.

FIG. 4 shows a further embodiment of a moulding pin (6). In this embodiment, the moulding pin (6) has a frustoconical end region (10), a cylindrical reduced region (13), and a cylindrical longitudinal region (11). In this case, the regions have a circular cross section. The longitudinal region (11) furthermore has a first diameter (12) which is larger than the second diameter (14) of the reduced region. The moulding pin (6) can thus be fastened at the longitudinal region (11) thereof, and, at the same time, the reduced region (13) can form a channel (9) having a smaller diameter. The reduced region (13) can extend over the entire length of the channel (9), whereby a channel (9) having a constant diameter would be formed. It would also be conceivable, however, for the reduced region (13) to extend over only a section of the channel length. Accordingly, a channel (9) having two different diameters would be formed. In addition, the moulding pin (6) has a transition region (19) between the longitudinal region (11) and the reduced region (13). The diameter of the moulding pin (6) preferably tapers continuously in said transition region (19).

Figure 5:
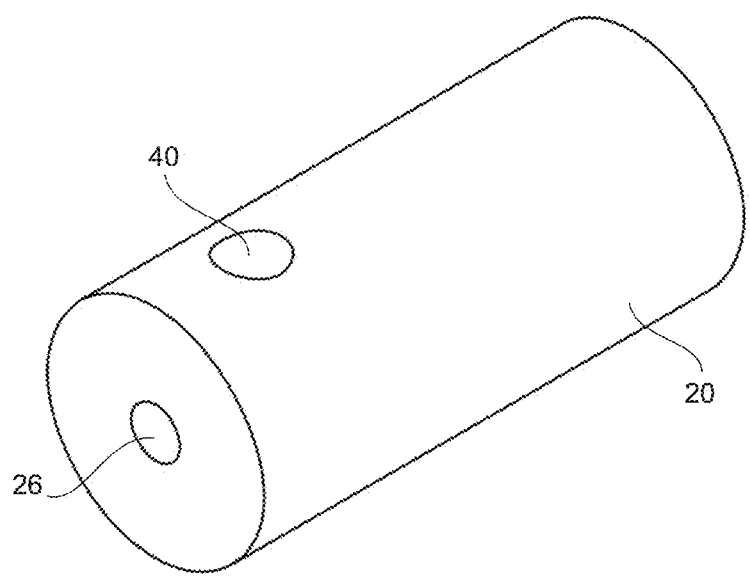
FIG. 5 is an isometric view of a fixing unit known from the prior art.
Figure 6:
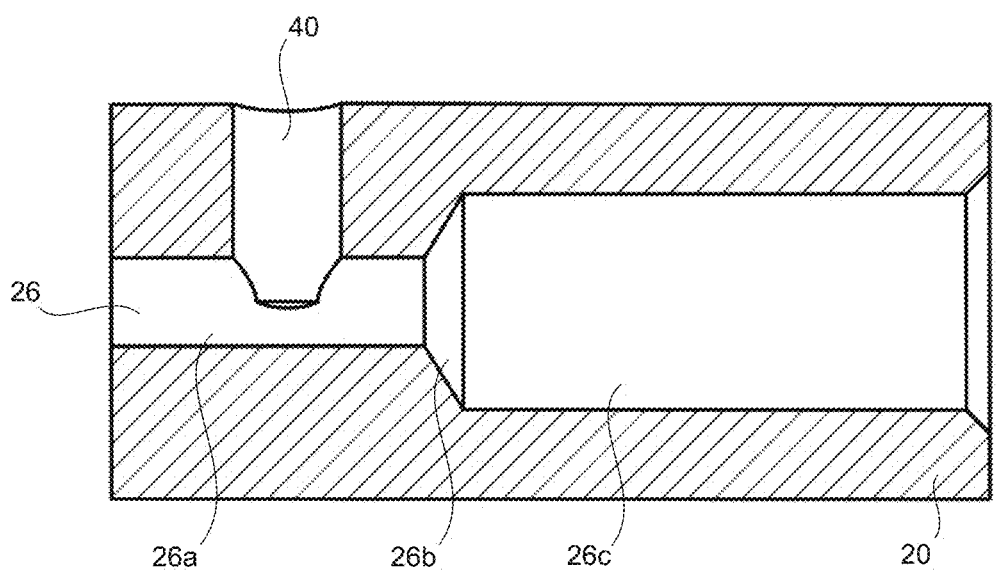
FIG. 6 is a sectional view of a fixing unit known from the prior art.
Figure 7:
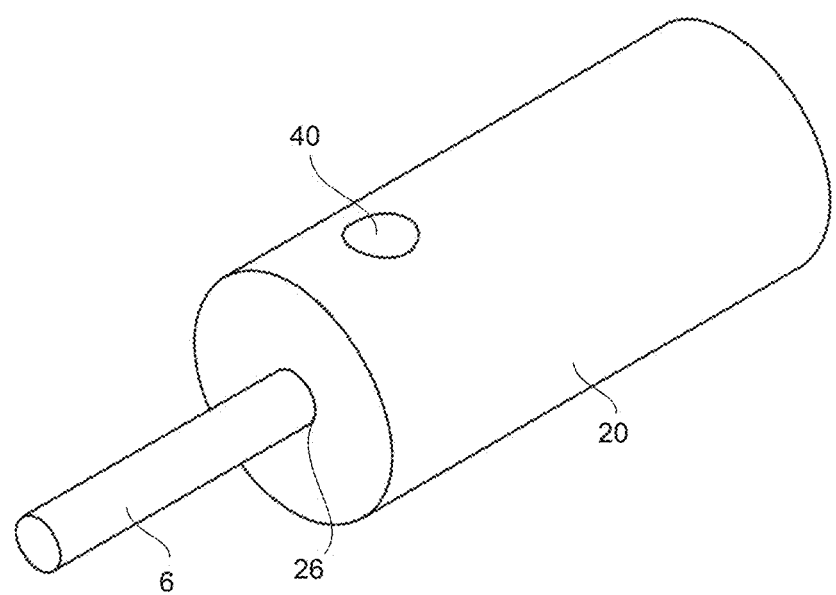
FIG. 7 is an isometric view of a fixing unit known from the prior art, comprising a moulding pin arranged therein.
Figure 8:
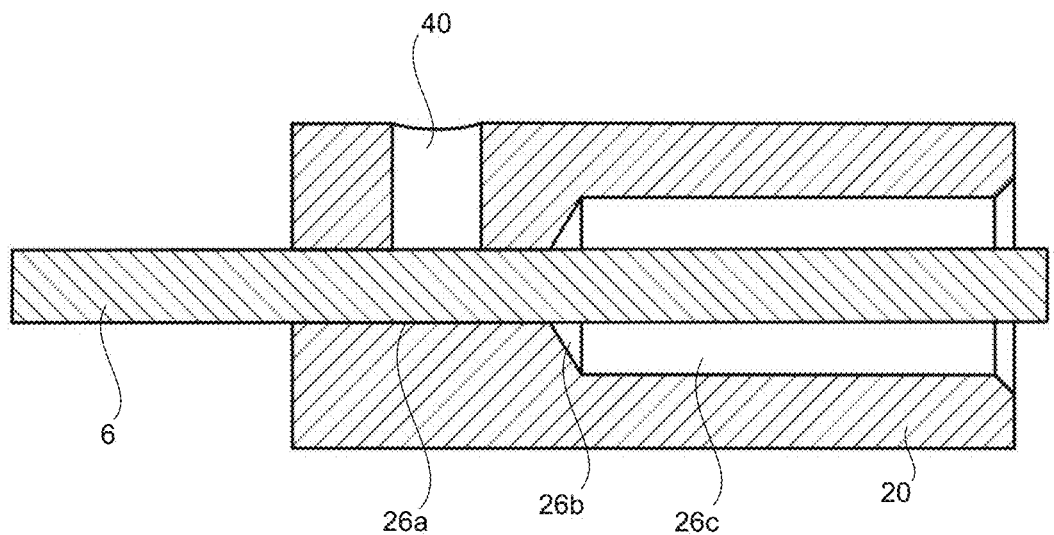
FIG. 8 is a sectional view of a fixing unit known from the prior art, comprising a moulding pin arranged therein.

FIGS. 5 to 8 show a fixing unit (20) known from the prior art. FIG. 5 is an isometric view of a fixing unit (20) known from the prior art, FIG. 6 is a sectional view of the fixing unit (20), FIG. 7 is an isometric view of the fixing unit (20) comprising a moulding pin (6) arranged therein, and FIG. 8 is a sectional view of the fixing unit (20) comprising a moulding pin (6) arranged therein.

The cylindrical fixing unit (20) has a through bore (26) in which the moulding pin (6) is arranged. Said through bore (26) in turn has a first region (26a) in which the inner diameter of the through bore (26) approximately corresponds to or is slightly larger than the outer diameter of the moulding pin (6). A bore (40), in which a fixing screw can be arranged, leads into said first region (26a). The moulding pin (6) is point fixed by means of a fixing screw of this kind. If more brittle moulding pins (6) are used, point loading of this kind can lead to the moulding pin (6) breaking. The through bore (26) further has a second region (26c) in which the inner diameter of the through bore (26) is significantly larger than the outer diameter of the moulding pin (6). A tool can be inserted in this region in order to exchange the moulding pin (6). The first region (26a) is connected to the second region (26c) via a transition region (26b). In said transition region, the inner diameter of the second region (26c) reduces continuously, to the inner diameter of the first region (26a).

Figure 9:
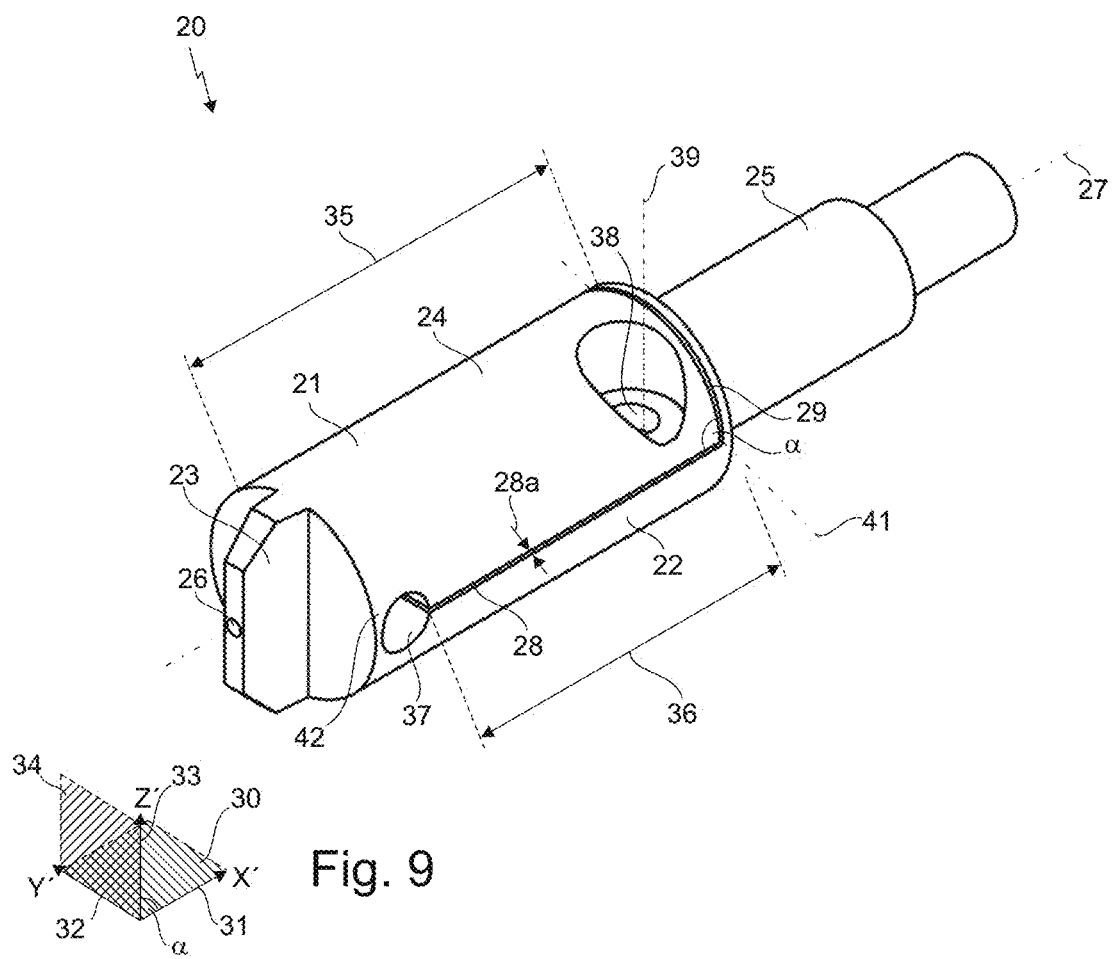
FIG. 9 is an isometric view of a fixing unit according to a first embodiment.
Figure 10:
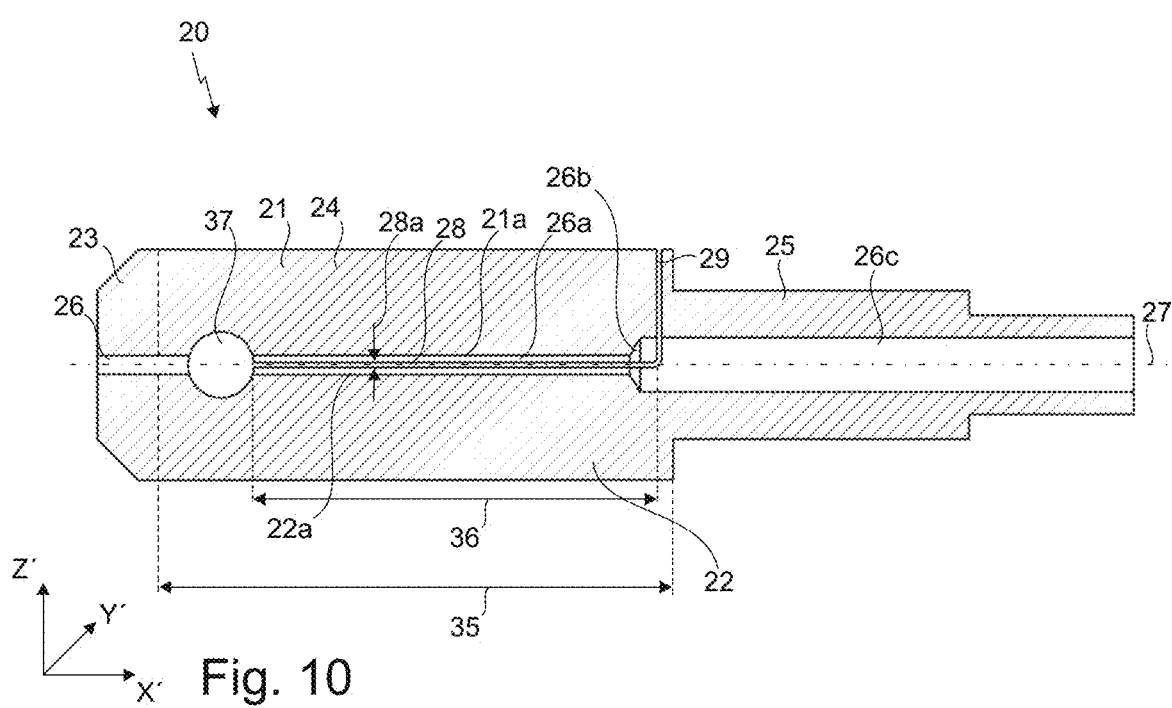
FIG. 10 is a sectional view of a fixing unit according to a first embodiment.
Figure 11:
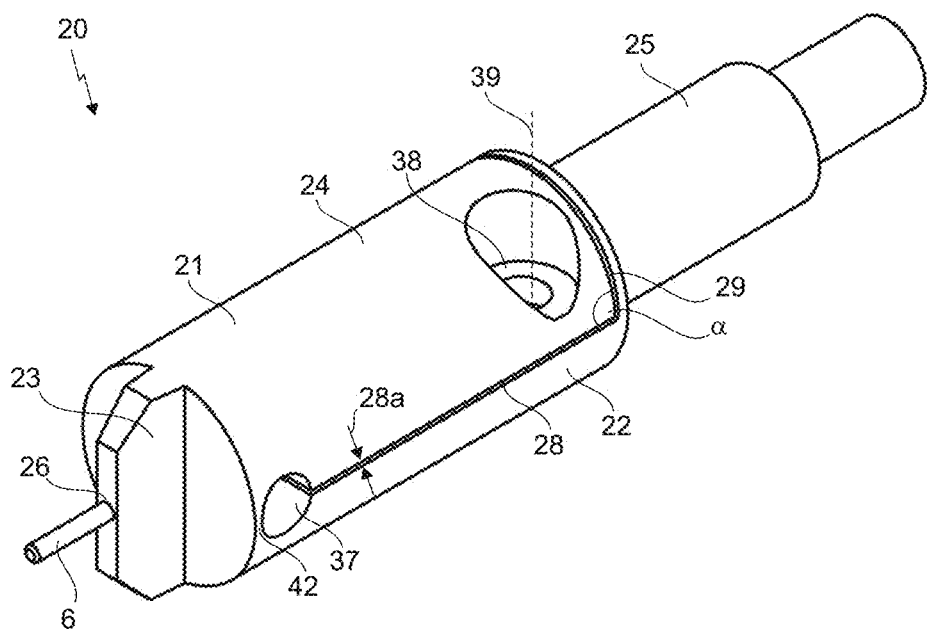
FIG. 11 is an isometric view of a fixing unit according to a first embodiment, comprising a moulding pin arranged therein.
Figure 12:
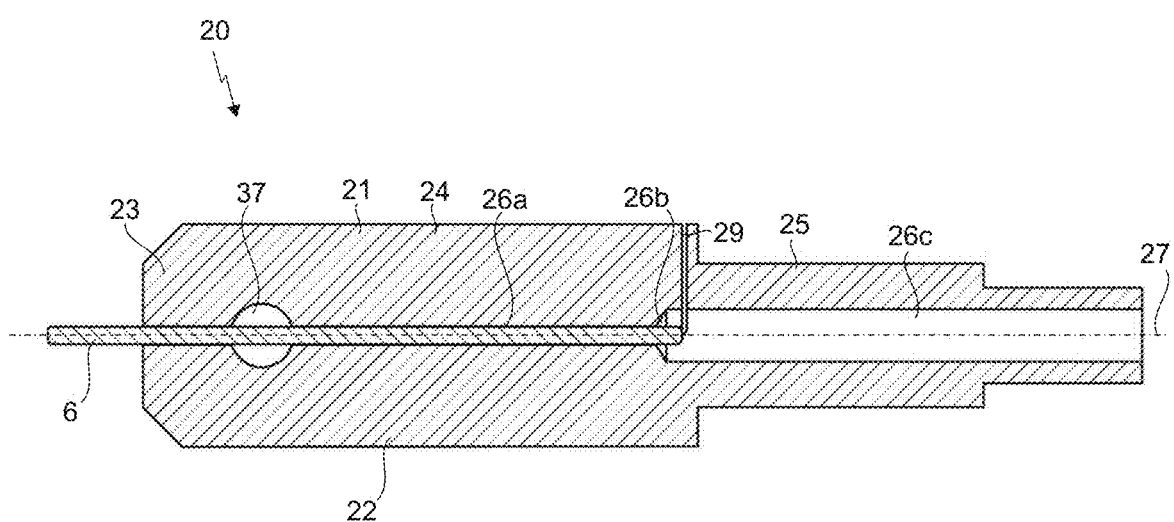
FIG. 12 is a sectional view of a fixing unit according to a first embodiment, comprising a moulding pin arranged therein.
Figure 17:
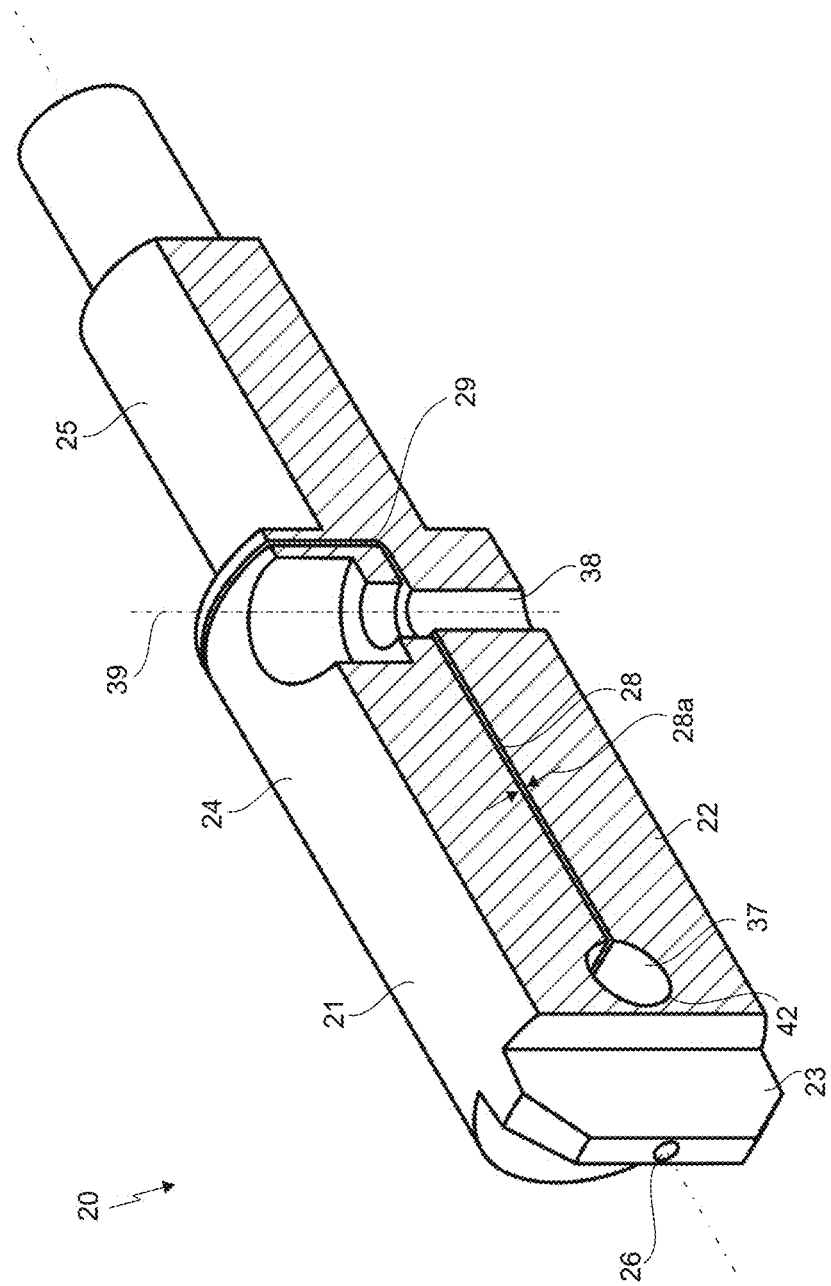
FIG. 17 is a sectional view of a fixing unit.

FIGS. 9 to 11 show a fixing unit (20) according to a first embodiment, having two jaw-type elements (21, 22) which can be pressed extensively on the moulding pin (6), whereby the moulding pin (6) is force-lockingly fixed, the jaw-type elements (21, 22) of the fixing unit (20) being formed in one piece. In this case, FIG. 9 is an isometric view of the fixing unit (20), FIG. 10 is a sectional view of the fixing unit (20), FIG. 11 is an isometric view of the fixing unit (20) comprising a moulding pin (6) arranged therein, and FIG. 12 is a sectional view of the fixing unit (20) comprising a moulding pin (6) arranged therein. FIG. 17 is furthermore an isometric view of the fixing unit (20) having an off-centre cross section.

The fixing unit (20) extends along an axial direction (X') and in the process has a first section (23), a second section (24) that is formed as a circular cylinder, and a third section (25) that is formed as a circular cylinder. The first section (23) is a cuboid and has lateral faces that are slanted towards the opening of the through bore. The fixing unit (20) has a first through bore (26) which extends along an axial central axis (27) of the fixing unit (20) and in which the moulding pin (6) can be arranged at least in sections, the moulding pin (6) being able to be arranged in such a way as to protrude beyond the first section (23). Said protruding section is moved via the open end (3a) of the glass blank (3) in the moulded section (4) when the moulded section (4) of said glass blank is deformed. The moulded section (4) is then deformed by the second moulding tool (7, 7a, 7b) in such a way that an inner surface (8) of the moulded section (4) is in contact with the section of the moulding pin (6) located in the moulded section (4), whereby the moulded section (4) of the glass blank (3) forms a channel (9).

The second section (24) has a first length (35) along the axial direction (X'). The jaw-type elements (21, 22) are spaced apart in the second section by means of a first (28) and a second slot (29). The first slot (28) is arranged in a first plane (30) that is spanned by a first vector (31) in the axial direction (X') and by a second vector (32) in the radial direction (Y'). The second slot (29) is arranged in a second plane (34) that is spanned by the second vector (32) and by a third vector (33). The third vector (33) and the first plane (30) enclose an angle α. In this embodiment, the angle α is 90°. The first (28) and the second slot (29) have a common intersection line (41) which extends along the radial direction (Y'). The first slot (28) has a second length (36) along the axial direction (X') that is less than the first length (35) of the second section (24).

The fixing unit (20) has a second through bore (37) in the second section (24), which bore extends in the radial direction (Y'), the second through bore (37) being open towards the first slot (28) and being arranged between the first section (23) of the fixing unit (20) and the first slot (28) in the axial direction. The second section (24) further has a connecting region (42) in which the two jaw-type elements (21, 22) are interconnected.

Furthermore, the second section (24) has a third through bore (38), the central axis (39) of which is perpendicular on the first plane (30) and is radially off-centre with respect to the axial central axis (27) of the fixing unit (20). A fastening means can be fastened in the third through bore (38), which fastening means can reduce a slot width (28a) of the first slot (28), whereby the jaw-type elements (21, 22) can be pressed on the moulding pin (6). A fastening means of this kind could be a clamping screw for example, by means of which a force is applied to the two jaw-type elements (21, 22) such that said elements are pressed together, whereby the moulding pin (6) is fixed extensively by the jaw-type elements (21, 22). The through bore further has a depression in which a clamping screw of this kind can be arranged. The off-centre arrangement of the third through bore (38) does not impede the course of the first through bore (26) or of the moulding pin (6) arranged therein. Said off-centre arrangement of the third through bore (38) can be seen in FIG. 17.

The second through bore (37) promotes leverage between the jaw-type elements (21, 22). The spacing between the third through bore (38) and the second through bore (37) in the axial direction (X') is preferably selected so as to be as large as possible in order to achieve correspondingly large leverage.

The first through bore (26) has a first region (26a) in which the through bore (26) is formed in the jaw-type elements (21, 22). Accordingly, in said first region (26a), the through bore (26) is defined by the contact surfaces (21a, 22a) of the jaw-type elements (21, 22). Said contact surfaces (21a, 22a) can be pressed on the moulding pin (6), whereby said pin is fixed extensively. The through bore (26) further has a second region (26c) in which the inner diameter of the through bore (26) is significantly larger than the outer diameter of the moulding pin (6). A tool can be inserted in this region in order to exchange the moulding pin (6). The first region (26a) is connected to the second region (26c) via a transition region (26b). In said transition region, the inner diameter of the second region (26c) reduces continuously, to the inner diameter of the first region (26a).

FIGS. 9 to 11 show a fixing unit (20) according to a first embodiment, having two jaw-type elements (21, 22) which can be pressed extensively on the moulding pin (6), whereby the moulding pin (6) is force-lockingly fixed, the jaw-type elements (21, 22) of the fixing unit (20) being formed in one piece. In this case, FIG. 9 is an isometric view of the fixing unit (20), FIG. 10 is a sectional view of the fixing unit (20), FIG. 11 is an isometric view of the fixing unit (20) comprising a moulding pin (6) arranged therein, and FIG. 12 is a sectional view of the fixing unit (20) comprising a moulding pin (6) arranged therein.

FIGS. 13 to 16 show a fixing unit (20) according to a further embodiment, having two jaw-type elements (21, 22) which can be pressed extensively on the moulding pin (6), whereby the moulding pin (6) is force-lockingly fixed, the jaw-type elements (21, 22) of the fixing unit (20) being formed in one piece. In the following, only the differences from the first embodiment will be set out. With regard to identical features, reference is made to the first embodiment.

Figure 13:
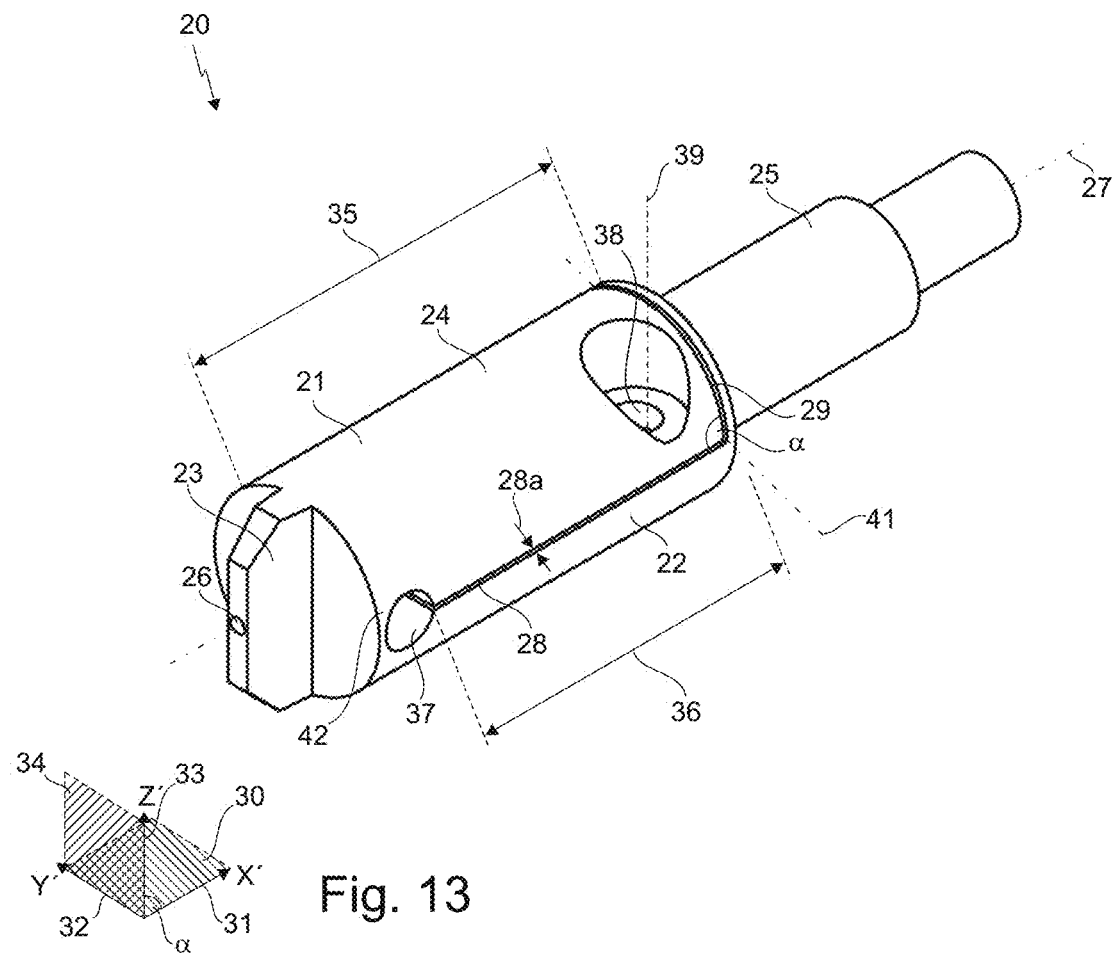
FIG. 13 is an isometric view of a fixing unit according to a further embodiment.
Figure 14:
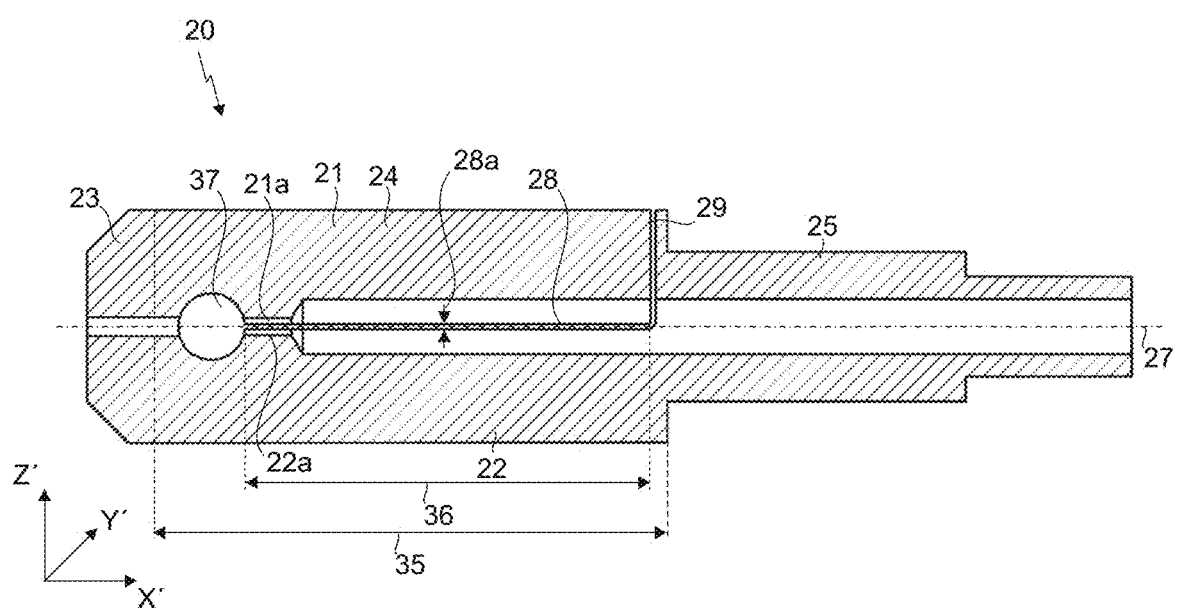
FIG. 14 is a sectional view of a fixing unit according to a further embodiment.
Figure 15:
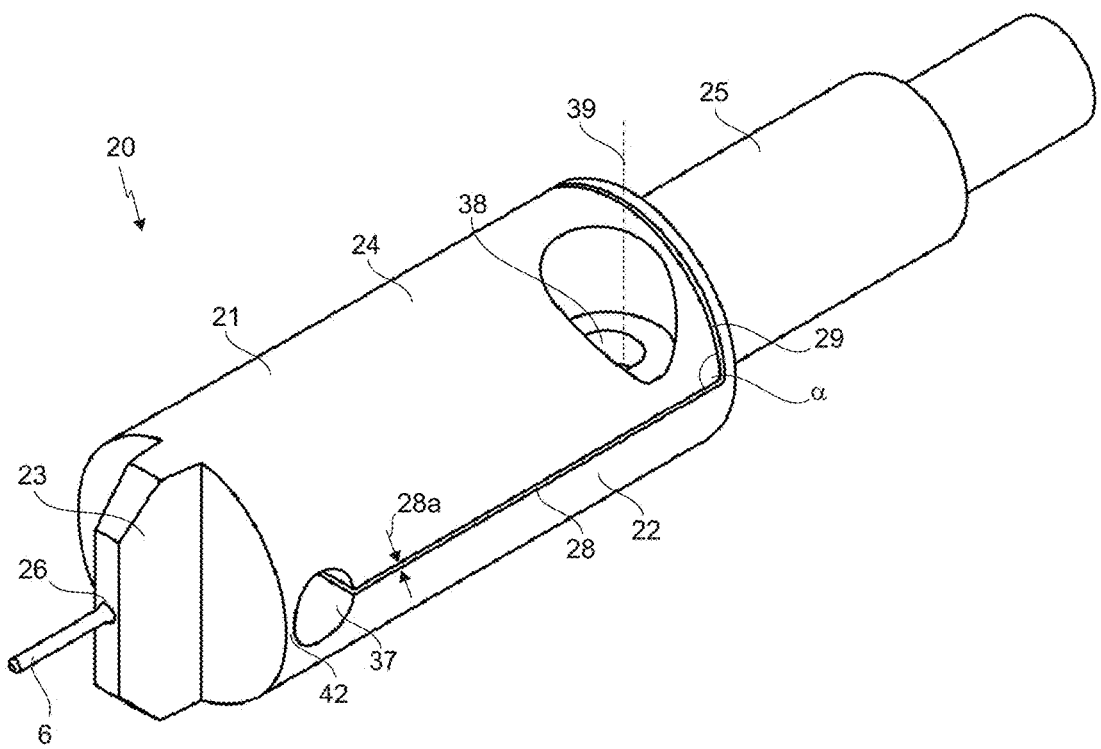
FIG. 15 is an isometric view of a fixing unit according to a further embodiment, comprising a moulding pin arranged therein.
Figure 16:
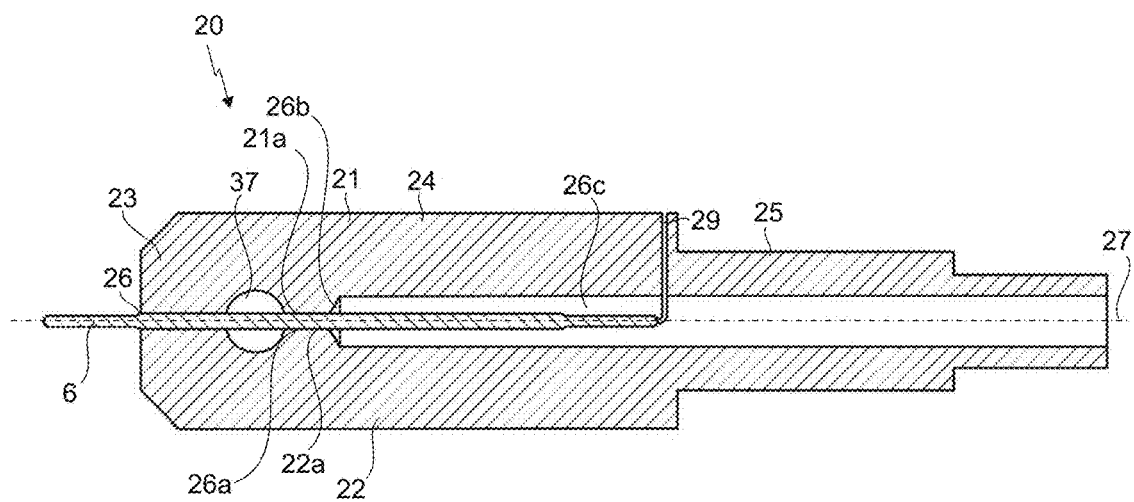
FIG. 16 is a sectional view of a fixing unit according to a further embodiment, comprising a moulding pin arranged therein.

FIG. 13 is an isometric view of the fixing unit (20) that is similar to FIG. 9 of the first embodiment. FIG. 14 is a sectional view of the fixing unit (20) that is similar to FIG. 10 of the first embodiment. FIG. 15 is an isometric view of the fixing unit (20) comprising a moulding pin (6) arranged therein that is similar to FIG. 11 of the first embodiment. FIG. 16 is a sectional view of the fixing unit (20) comprising a moulding pin (6) arranged therein that is similar to FIG. 12 of the first embodiment.

The difference between this embodiment and the first embodiment can be seen in the sectional views in FIGS. 14 and 16 and is that the length of the first region (26a) of the through bore (26) along the axial direction (X') is smaller. Accordingly, the length of the contact surfaces (21a, 22a) which can be pressed on the moulding pin (6) and by means of which the moulding pin (6) is fixed extensively is also smaller. A fixing unit (20) of this kind is advantageous when moulding pins (6) having a reduced region (13), as described in FIG. 4 for example, are used. The contact surfaces (21a, 22a) would thus only be in contact with the longitudinal region (11) of the moulding pin (6) that has a larger diameter (12) than the reduced region (13).

FIG. 18 and FIG. 18a schematically show two possible embodiments of medical glass containers (2) which were produced by means of a device (1) according to the invention and/or a method according to the invention. The medical glass container (2) has an end piece formed from the moulded section (4) of the hollow cylindrical glass blank (2). In the embodiment shown in FIG. 18a, the end piece has a projection that can be used for fastening needle protectors.

FIG. 19 shows microscope images of moulding pins (6). FIG. 19a shows a new tungsten moulding pin (6). FIG. 19b shows said moulding pin (6) after a production time of 1 hour. Serious abrasion of the moulding pin (6) can be clearly identified here. FIG. 19c shows a new silicon nitride moulding pin (6). FIG. 19d shows said moulding pin (6) after a production time of 2.5 hours. It can be seen from these drawings that the silicon nitride moulding pin is subject to significantly less abrasion than the tungsten moulding pin.

Analyses, using a ICP-MS Xs instrument, of glass syringe bodies produced from silicon nitride or glass-like carbon revealed a tungsten content of 2 orders of magnitude lower than the measured tungsten content of glass syringe bodies produced using tungsten moulding pins.

All the features disclosed in the application documents are claimed as essential to the invention, if said features are novel over the prior art, either individually or in combination.

LIST OF REFERENCE SIGNS 1 device for producing a medical glass container
2 medical glass container
3 hollow cylindrical glass blank
3a open end of the hollow cylindrical glass blank
4 moulded section
5 first moulding tool
6 moulding pin
7 second moulding tool
7a, 7b shaping rollers
8 inner surface of the moulded section
9 channel
10 frustoconical end region of the moulding pin
11 longitudinal region of the moulding pin
12 first diameter
13 reduced region of the moulding pin
14 second diameter
15 retaining device
16 axial central axis of the glass blank
17 first spacing between the shaping rollers
18 second spacing between the shaping rollers
19 transition region
20 fixing unit
21 first jaw-type element
21a contact surface of the first jaw-type element
22 second jaw-type element
22a contact surface of the second jaw-type element
23 first section of the fixing unit
24 second section of the fixing unit
25 third section of the fixing unit
26 first through bore of the fixing unit
26a first region of the first through bore of the fixing unit
26b transition region of the first through bore of the fixing unit
26c second region of the first through bore of the fixing unit
27 axial central axis of the fixing unit
28 first slot
28a slot width of the first slot
29 second slot
30 first plane
31 first vector
32 second vector
33 third vector
34 second plane
35 first length
36 second length
37 second through bore
38 third through bore
39 central axis of the third through bore
40 bore
41 intersection line
42 connecting region

The invention claimed is:

1. A device for producing a high-purity medical glass container from a hollow cylindrical glass blank extending along an axial direction (X) and having at least one open end, the glass blank having a moulded section extending in the axial direction (X) from the open end, wherein said section is in a mouldable state, the device comprising:
   a. a first moulding tool having a moulding pin, the moulding pin being able to be moved via the open end of the hollow cylindrical glass blank in the moulded section thereof along the axial direction (X), the moulding pin being fixed in a fixing unit of the first moulding tool;
   b. a second moulding tool, wherein at least the moulded section is able to be deformed by the second moulding tool in such a way that an inner surface of the moulded section is in contact with the moulding pin; whereby the moulded section forms a channel,
wherein,
the fixing unit has at least two jaw-type elements able to be pressed extensively on the moulding pin, whereby the moulding pin is able to be force-lockingly fixed, wherein the moulding pin consists of a non-metallic material,
wherein the fixing unit extends along an axial direction (X') and has a first section, a second section, and a third section, and
wherein the second section has a first and a second slot, the jaw-type elements being spaced apart by means of the first and the second slot, the first slot being arranged in a first plane that is spanned by a first vector in the axial direction (X') and by a second vector in the radial direction (Y'), the second slot being arranged in a second plane that is spanned by the second vector and by a third vector, the third vector and the first plane enclosing an angle α, the first and the second slot having a common intersection line which extends along the radial direction (Y').

2. The device according to claim 1, wherein the jaw-type elements of the fixing unit are formed in one piece.

3. The device according to claim 1, wherein the second section and the third section are formed as a circular cylinder, the fixing unit having a first through bore that extends along an axial central axis of the fixing unit and in which the moulding pin is able to be arranged at least in sections, the moulding pin being able to be arranged so as to protrude beyond the first section.

4. The device according to claim 3, wherein the fixing unit has a second through bore in the second section, said bore extending in the radial direction (Y'), the second through bore being open towards the first slot and being arranged between the first section of the fixing unit and the first slot in the axial direction.

5. The device according to claim 3, wherein the second section has a third through bore, the central axis of which is perpendicular to the first plane and is radially off-centre with respect to the axial central axis of the fixing unit, it being possible for a fastening means to be fastened in the third through bore, said fastening means able to reduce a slot width of the first slot, whereby the jaw-type elements are able to be pressed on the moulding pin.

6. The device according to claim 1, wherein the second section has a first length along the axial direction (X'), the first slot having a second length along the axial direction (X') that is smaller than the first length.

7. The device according to claim 1, wherein the moulding pin consists of technical ceramics.

8. The device according to claim 1, wherein the moulding pin consists of a silicon nitride ($Si_3N_4$) or glass-like carbon.

9. The device according to claim 1, wherein the moulding pin has a frustoconical end region and a cylindrical longitudinal region having a circular cross section, the moulding pin having a constant first diameter in the longitudinal region, the first diameter being in a range of between 0.7 mm and 1.3 mm.

10. The device according to claim 1, wherein the moulding pin has a frustoconical end region, a cylindrical reduced region, and a cylindrical longitudinal region, the reduced region and the longitudinal region having a circular cross section, the longitudinal region having a first diameter which is larger than the second diameter of the reduced region, the first diameter being in a range of between 0.7 and 1.3 mm, and the second diameter being in a range of between 0.45 mm and 0.9 mm.

11. The device according to claim 1, wherein the second moulding tool has two mutually spaced shaping rollers, the shaping rollers being spaced apart by a first spacing when in a first position, it being possible for at least the moulded section of the hollow cylindrical glass blank to be moved between the shaping rollers when the shaping rollers are in the first position.

12. The device according to claim 11, wherein the shaping rollers are able to be moved into a second position in which said rollers are spaced apart by a second spacing that is smaller than the first spacing, the shaping rollers being able to apply a deformation force to the moulded section of the hollow cylindrical glass blank when in the second position, whereby an outer shaping of the moulded section is able to be achieved, it being possible for an inner shaping of the moulded section to be achieved by means of the moulding pin of the first moulding tool.

13. The device according to 1, wherein the medical glass container is a syringe or an ampoule or a carpule.

14. A method for producing a medical glass container having high-purity inner surfaces, said method comprising the following steps:
 a. providing a hollow cylindrical glass blank extending along an axial direction (X) and having at least one open end, the glass blank having a mouldable moulded section extending in the axial direction (X) from the open end;
 b. providing a first moulding tool having a moulding pin, the moulding pin being fixed in a fixing unit of the first moulding tool;
 c. providing a second moulding tool, via which at least the moulded section of the hollow cylindrical glass blank is able to be deformed;
 d. inserting the moulding pin via the open end of the hollow cylindrical glass blank in the moulded section thereof;
 e. deforming the moulded section by the second moulding tool in such a way that an inner surface of the moulded section is in contact with the moulding pin, whereby the moulded section forms a channel;
wherein
the fixing unit has at least two jaw-type elements which are able to be pressed extensively on the moulding pin, whereby the moulding pin is force-lockingly fixed, wherein the moulding pin consists of a non-metallic material,
wherein the fixing unit extends along an axial direction (X') and has a first section, a second section, and a third section, and
wherein the second section has a first and a second slot, the jaw-type elements being spaced apart by means of the first and the second slot, the first slot being arranged in a first plane that is spanned by a first vector in the axial direction (X') and by a second vector in the radial direction (Y'), the second slot being arranged in a second plane that is spanned by the second vector and by a third vector, the third vector and the first plane enclosing an angle α, the first and the second slot having a common intersection line which extends along the radial direction (Y').

15. The method according to claim 14, wherein the medical glass container is a syringe or an ampoule or a carpule.

16. The method according to claim 14, wherein the second section has a first length along the axial direction (X'), the first slot having a second length along the axial direction (X') that is smaller than the first length.

17. The method according to claim 14, wherein the fixing unit has a second through bore in the second section, said bore extending in the radial direction (Y'), the second through bore being open towards the first slot and being arranged between the first section of the fixing unit and the first slot in the axial direction.

18. The method according to claim 14, wherein the second section and the third section are formed as a circular cylinder, the fixing unit having a first through bore that extends along an axial central axis of the fixing unit and in which the moulding pin is able to be arranged at least in sections, the moulding pin being able to be arranged so as to protrude beyond the first section.

19. A device for producing a high-purity medical glass container from a hollow cylindrical glass blank extending along an axial direction (X) and having at least one open end, the glass blank having a moulded section extending in the axial direction (X) from the open end, wherein said section is in a mouldable state, the device comprising:
 a. a first moulding tool having a moulding pin, the moulding pin being able to be moved via the open end of the hollow cylindrical glass blank in the moulded section thereof along the axial direction (X), the moulding pin being fixed in a fixing unit of the first moulding tool;
 b. a second moulding tool, wherein at least the moulded section is able to be deformed by the second moulding tool in such a way that an inner surface of the moulded section is in contact with the moulding pin, whereby the moulded section forms a channel,
wherein,
the fixing unit has at least two jaw-type elements able to be pressed extensively on the moulding pin, whereby the moulding pin is able to be forcelockingly fixed, wherein the moulding pin consists of a non-metallic material,
wherein the fixing unit extends along an axial direction (X') and has a first section, a second section, and a third section, the fixing unit having a first through bore that extends along an axial central axis of the fixing unit and in which the moulding pin is able to be arranged at least in sections, and wherein the first section is a cuboid and has lateral faces that are slanted towards the opening of the first through bore, the moulding pin being able to be arranged in such a way as to protrude beyond the first section.

20. A method for producing a medical glass container having high-purity inner surfaces, said method comprising the following steps:

a. providing a hollow cylindrical glass blank extending along an axial direction (X) and having at least one open end, the glass blank having a mouldable moulded section extending in the axial direction (X) from the open end;
b. providing a first moulding tool having a moulding pin, the moulding pin being fixed in a fixing unit of the first moulding tool;
c. providing a second moulding tool, via which at least the moulded section of the hollow cylindrical glass blank is able to be deformed;
d. inserting the moulding pin via the open end of the hollow cylindrical glass blank in the moulded section thereof; e. deforming the moulded section by the second moulding tool in such a way that an inner surface of the moulded section is in contact with the moulding pin, whereby the moulded section forms a channel;

wherein
the fixing unit has at least two jaw-type elements which are able to be pressed extensively on the moulding pin, whereby the moulding pin is forcelockingly fixed, wherein the moulding pin consists of a non-metallic material, and
wherein the fixing unit extends along an axial direction (X') and has a first section, a second section, and a third section, the fixing unit having a first through bore that extends along an axial central axis of the fixing unit and in which the moulding pin is able to be arranged at least in sections, wherein the first section is a cuboid and has lateral faces that are slanted towards the opening of the first through bore, the moulding pin being able to be arranged in such a way as to protrude beyond the first section.

\* \* \* \* \*